(12) United States Patent
Domansky et al.

(10) Patent No.: US 10,836,987 B2
(45) Date of Patent: Nov. 17, 2020

(54) MICROFLUIDIC DEVICE HAVING OFFSET, HIGH-SHEAR SEEDING CHANNELS

(71) Applicant: President and Fellows of Harvard College, Cambridge, MA (US)

(72) Inventors: Karel Domansky, Charlestown, MA (US); Christopher David Hinojosa, Cambridge, MA (US); Donald E. Ingber, Boston, MA (US); Daniel Levner, Brookline, MA (US); Guy Thompson, II, Watertown, MA (US)

(73) Assignee: PRESIDENT AND FELLOWS OF HARVARD COLLEGE, Cambridge, MA (US)

(*) Notice: Subject to any disclaimer, the term of this patent is extended or adjusted under 35 U.S.C. 154(b) by 214 days.

(21) Appl. No.: 15/566,566

(22) PCT Filed: Apr. 8, 2016

(86) PCT No.: PCT/US2016/026831
§ 371 (c)(1),
(2) Date: Oct. 13, 2017

(87) PCT Pub. No.: WO2016/168091
PCT Pub. Date: Oct. 20, 2016

(65) Prior Publication Data
US 2018/0119081 A1   May 3, 2018

Related U.S. Application Data

(60) Provisional application No. 62/147,316, filed on Apr. 14, 2015.

(51) Int. Cl.
| | | |
|---|---|---|
| *C12M 3/06* | (2006.01) | |
| *C12M 1/34* | (2006.01) | |
| *C12M 1/42* | (2006.01) | |
| *B01L 3/00* | (2006.01) | |
| *C12M 1/12* | (2006.01) | |
| *C12M 1/00* | (2006.01) | |

(52) U.S. Cl.
CPC .......... *C12M 23/16* (2013.01); *B01L 3/5027* (2013.01); *C12M 25/02* (2013.01); *C12M 29/14* (2013.01); *C12M 35/04* (2013.01); *C12M 35/08* (2013.01); *C12M 41/00* (2013.01); *B01L 2300/0864* (2013.01); *B01L 2300/0867* (2013.01); *B01L 2300/0887* (2013.01)

(58) Field of Classification Search
CPC ............ B01L 23/16; B01L 2300/0863; B01L 2300/0867; B01L 2300/0887; C12M 23/16; C12M 29/14; C12M 35/04; C12M 35/08; C12M 41/00
See application file for complete search history.

(56) References Cited

U.S. PATENT DOCUMENTS

| | | | | |
|---|---|---|---|---|
| 2009/0004737 | A1* | 1/2009 | Borenstein | ........ B01L 3/502707 435/395 |
| 2011/0082563 | A1 | 4/2011 | Charest | |
| 2011/0250585 | A1* | 10/2011 | Ingber | .................... C12N 5/061 435/5 |
| 2014/0065660 | A1 | 3/2014 | Kim | |

FOREIGN PATENT DOCUMENTS

WO   WO 2015/138034 A2   9/2015

OTHER PUBLICATIONS

Rupprecht et al. "A tapered channel microfluidic device for comprehensive cell adhesion analysis, using measurements of detachment kinetics and shear stress-dependent motion" Biomicrofluidics 6, 014107 (2012) (Year: 2012).*
Dictionary.com "layer" 1 page, accessed on Jul. 5, 2020 (Year: 2020).*
Green et al. "Microfluidic enrichment of a target cell type from a heterogenous suspension by adhesion-based negative selection" Lab Chip, 2009, 9, 2245-2248 (Year: 2009).*
Plouffe et al. "Peptide-Mediated Selective Adhesion of Smooth Muscle and Endothelial Cells in Microfluidic Shear Flow" Langmuir 2007, 23, 5050-5055 (Year: 2007).*
Woo Kwon et al. "Label-free, microfluidic separation and enrichment of human breast cancer cells by adhesion difference" Lap Chip, 2007, 7, 1461-1468 (Year: 2007).*
Didar et al., "Adhesion based detection, sorting and enrichment of cells in microfluidic Lab-on-Chip devices," Lab Chip, Nov. 21, 2010, vol. 10, No. 22, pp. 3043-3053.
Lu et al., "Microfluidic shear devices for quantitative analysis of cell adhesion," Anal. Chem. 15, Sep. 15, 2004, vol. 76, No. 18, pp. 5257-5264.
Christ et al., "Methods to Measure the Strength of Cell Adhesion to Substrates," Journal of Adhesion Science and Technology, 24 pp. 2027-2058, 2010 (33 pages).
Manbachi et al., "Micrcirculation within grooved substrates regulates cell positioning and cell docking inside microfluidic channels," Lab on a Chip, The Royal Society of Chemistry, pp. 747-754, 2008 (8 pages).

(Continued)

*Primary Examiner* — Thane Underdahl
(74) *Attorney, Agent, or Firm* — Nixon Peabody LLP

(57) ABSTRACT

A microfluidic device for determining a response of cells comprises a microchannel and a seeding channel. The microchannel is at least partially defined by a porous membrane having cells adhered thereto. The microchannel has a first cross-sectional area. The seeding channel delivers a working fluid to the cells within the microchannel. The seeding channel has a second cross-sectional area that is less than the first cross-sectional area such that a flow of the working fluid produces a substantially higher shear force within the seeding channel to inhibit the attachment of cells within the seeding channel. And when multiple seeding channels are used to deliver fluids to multiple microchannels that define an active cellular layer across the membrane, the seeding channels are spatially offset from each other such that fluid communication between the fluids occurs only at the active region via the membrane, not at the seeding channels.

12 Claims, 4 Drawing Sheets

(56) References Cited

OTHER PUBLICATIONS

International Search Report in International Patent Application No. PCT/US2016/026831, dated Sep. 2, 2016 (4 pages).
Written Opinion in International Patent Application No. PCT/US2016/026831, dated Sep. 2, 2016 (14 pages).
Extended European Search Report in European Patent Application No. 16780500.1, dated Oct. 29, 2018 (10 pages).

* cited by examiner

MICROFLUIDIC DEVICE HAVING OFFSET, HIGH-SHEAR SEEDING CHANNELS

CROSS-REFERENCE TO RELATED APPLICATIONS

This application is a national stage of International Application No. PCT/US2016/026831, filed on Apr. 8, 2016, and titled "Microfluidic Device Having Offset, High-Shear Seeding Channels," which claims the benefit of and priority to U.S. Provisional Application No. 62/147,316, filed Apr. 14, 2015, and titled "Microfluidic Device Having Offset, High-Shear Seeding Channels," each of which is herein incorporated by reference in its entirety.

GOVERNMENT SUPPORT

This invention was made with government support under contract no. W911NF-12-2-0036 awarded by U.S. Department of Defense, Advanced Research Projects Agency. The government has certain rights in the invention.

TECHNICAL FIELD

The present invention relates to cell culture systems and fluidic systems. More specifically, the invention relates to a microfluidic device having high-shear seeding channels to minimize cell culturing within the seeding channels. Alternatively or in combination, the seeding channels are also offset from each other to minimize the communication between cells within the different channels.

BACKGROUND

In microfluidic devices that are designed for experimentation on cells, there is typically an "active area" at which the cell culturing and experimentation are performed. Other areas in the device serve other functions. It is often desirable to constrain the cells to the active area and avoid cells in the other areas. In one exemplary microfluidic devices having a membrane that separates two microchannels, it is desirable to have the cells retained in the membrane region of the device, where cells can communicate through the membrane. On the other hand, it is desirable to avoid cells in the various fluid inlet and outlet channels that lead to and from the membrane region. The inlet fluid channels may be used for seeding the devices with cells to cause them to grow on one or both sides of the membrane, as well as for perfusing the cells during culture. When cells are intended to grow on both sides of the membrane, the membrane has a "bilayer" active region. The inlet fluid channels that provide working fluid to the cells within the microfluidic device are often referred to as the "seeding channels."

If no special effort is taken to reduce cells within the regions outside the membrane region, the seeded cells may begin to build-up within the seeding channels with similar density to cells in the membrane region. Because the bilayer region is where the experimentation takes place, it is desirable to maintain the ratio of the cells in the bilayer region to the cells in the seeding channel as high as possible such that good cellular homogeneity is maintained in the assays. This is particularly important as the number of replicated bilayer regions on a single device is increased, which increases the required length of the seeding channels.

Furthermore, it is desirable to limit the biological communication within the device to the active region at which the cell layers are separated by a porous membrane. One way to accomplish this objective is to develop a membrane that is only porous within the active region and nonporous in other areas that would be in contact with the various seeding channels and exit channels associated with each active region. However, such membranes having variable porous regions can be more expensive and require precise alignment on the device. Thus, it is more desirable to use a consistently porous membrane. But, such membranes have a disadvantage in that there is a possibility for fluidic or biological cross-communication through the porous membrane in regions outside of the active region.

The present invention solves many of the problems associated with the prior art systems by providing a unique geometric configuration to the seeding channel to increase the fluidic shear force, which discourages cellular attachment within those seeding channels. It also substantially decreases the possibility of fluidic or biological cross-communication through the porous membrane in regions outside of the active region.

SUMMARY

According to one aspect of the present invention, a microfluidic device for determining a response of cells comprises a microchannel and a seeding channel. The microchannel is at least partially defined by a membrane having cells adhered thereto. The microchannel has a first cross-sectional geometry. The seeding channel delivers a working fluid to the cells within the microchannel. The seeding channel has a second cross-sectional geometry that is adapted to produce a higher shear rate in a flow of a working fluid than the first cross-sectional geometry of the first microchannel to inhibit the attachment of cells within the seeding channel.

According to another aspect of the present invention, a microfluidic device for determining a response of cells comprises at least one body portion and a membrane. The body portion at least partially defines a first microchannel, a second microchannel, a first seeding channel for delivering a first fluid to the first microchannel, and a second seeding channel for delivering a second fluid to the second microchannel. The membrane is located at an interface region between the first microchannel and the second microchannel. The membrane includes a first side facing toward the first microchannel and a second side facing toward the second microchannel. The first side has the cells adhered thereto. The first seeding channel has a cross-sectional geometry that is adapted to produce a higher shear rate than a cross-sectional geometry of the first microchannel in a flow of the first fluid to inhibit the formation of cells within the seeding channel. In one example, the first seeding channel has a cross-sectional area that is less than a cross-sectional area of the first microchannel, producing a substantially higher shear force within the seeding channel to inhibit the formation of cells within the seeding channel.

The present invention also relates to a method of removing extraneous cells within a microfluidic device that includes a microchannel at least partially defined by a surface having cells thereon and a seeding channel for delivering fluids to the cells on the surface. The microchannel has a first cross-sectional geometry and the seeding channel has a second cross-sectional geometry that is different from the first cross-sectional geometry. The method comprising (i) permitting a cell-culturing fluid to be exposed to the surface for a sufficient period of time to permit a desired layer of cells to adhere to the surface, and (ii) after the desired layer of cells has been achieved, increasing a flow rate of a fluid to produce a substantially higher shear rate within the seeding channel to remove extraneous cells from the seeding channel while leaving the desired layer of cells on the surface relatively undisturbed.

In a yet another embodiment, the present invention is a microfluidic device for determining a response of cells comprising a body and a porous membrane. The body at least partially defines a first microchannel, a second microchannel, a first seeding channel for delivering a first fluid to the first microchannel, and a second seeding channel for delivering a second fluid to the second microchannel. The porous membrane is in contact with the body and defines a portion of the first microchannel, a portion of the second microchannel, a portion of the first seeding channel, and a portion of the second seeding channel. The porous membrane has cells thereon that are exposed to the first microchannel. The porous membrane permits fluid communication between the first fluid and the second fluid only at an interface region between the first microchannel and the second microchannel.

In a yet another embodiment, the present invention is a microfluidic device for determining a response of cells comprising a porous membrane, a first microchannel, a second microchannel, a first seeding channel, and a second seeding channel. The first microchannel is partially defined by the porous membrane, which has cells thereon that are exposed to the first microchannel. The second microchannel is partially defined by the porous membrane. The second microchannel and the first microchannel are on opposing sides of an interface region of the porous membrane. The first seeding channel is partially defined by the porous membrane and delivers a first fluid to the first microchannel. The second seeding channel is partially defined by the porous membrane and delivering a second fluid to the second microchannel. The second seeding channel is spatially offset from the first seeding channel such that fluid communication between the first fluid and the second fluid only occurs at the interface region between the first microchannel and the second microchannel.

In yet a further embodiment, the present invention is a microfluidic device for determining a response of cells comprising a porous membrane and a body having a first body segment and a second body segment. The porous membrane has a first side and a second side, and is positioned between the first body segment and the second body segment such the first side of the porous membrane contacts the first body segment and the second side of the porous membrane contacts the second body segment. The body and the porous membrane define a plurality of active regions in which cells communicate across the porous membrane. Each of the plurality of active regions includes a first microchannel partially defined by the first body segment and a second microchannel partially defined by the second body segment. The body and the porous membrane further define a plurality of first seeding channels for delivering a first fluid to the first microchannels and a plurality of second seeding channels for delivering a second fluid to the second microchannels. Each of the plurality of first and second seeding channels are spatially offset from each other such that fluid communication between the first fluid and the second fluid occurs predominantly only at the plurality of active regions via the porous membrane.

These and other capabilities of the invention, along with the invention itself, will be more fully understood after a review of the following figures, detailed description, and claims.

BRIEF DESCRIPTION OF THE DRAWINGS

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

Figure 1:
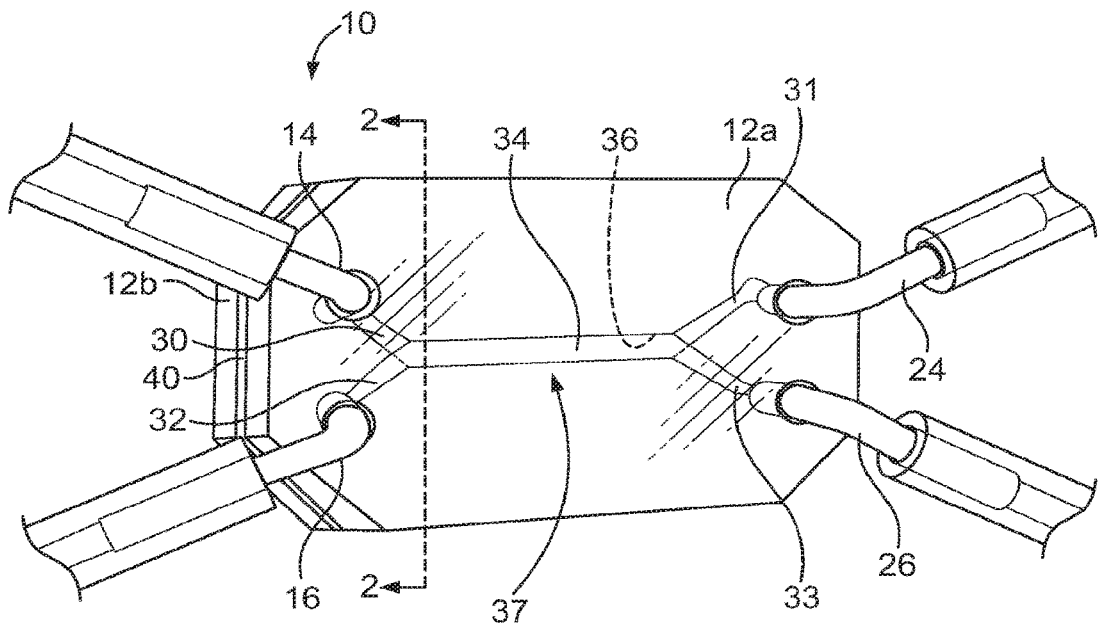
FIG. 1 illustrates an exemplary microfluidic device with a membrane region having cells thereon that may be used with the present invention.

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

The functionality of cells and tissue types (and even organs) can be implemented in one or more microfluidic devices or "chips" that enable researchers to study these cells and tissue types outside of the body while mimicking much of the stimuli and environment that the tissue is exposed to in-vivo. It can also be desirable to implement these microfluidic devices into interconnected components that can simulate groups of organs or tissue systems. Preferably, the microfluidic devices can be easily inserted and removed from an underlying fluidic system that connects to these devices in order to vary the simulated in-vivo conditions and organ systems.

Figure 2:
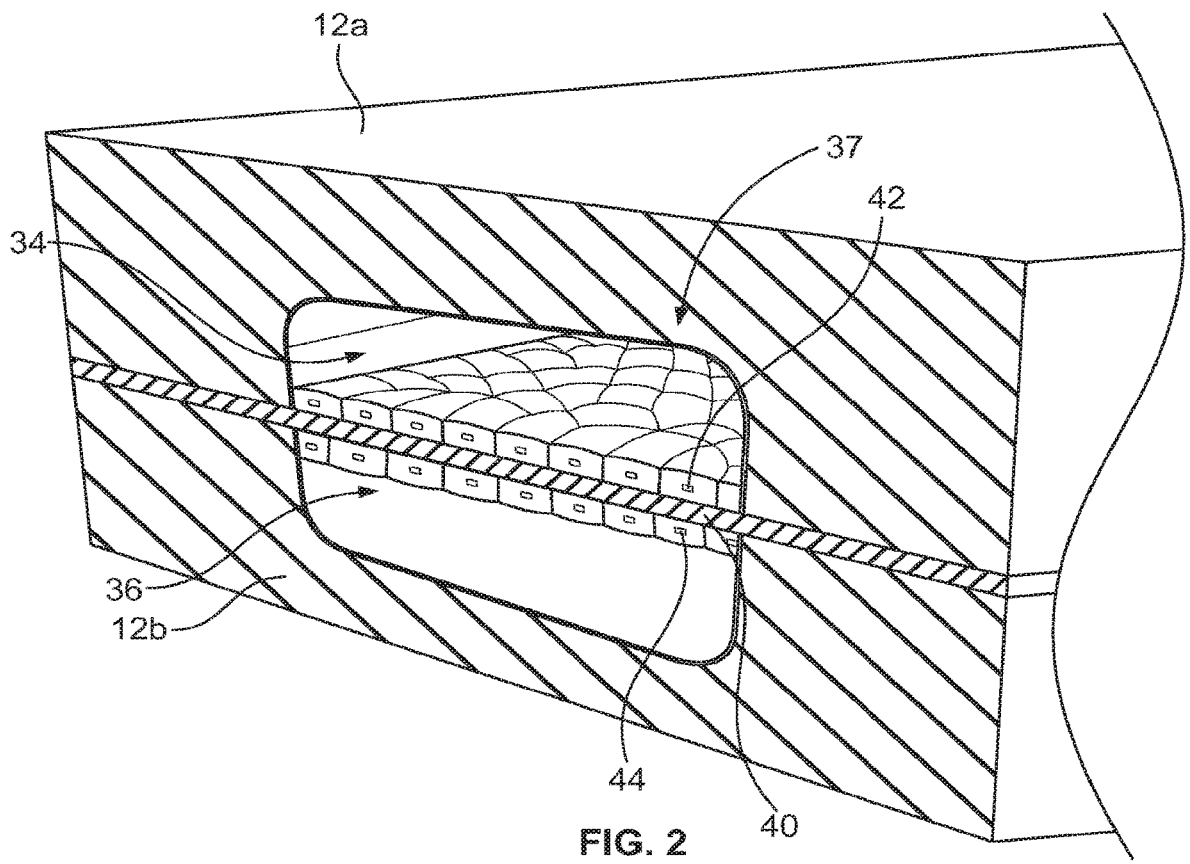
FIG. 2 is a cross-section of the microfluidic device taken along line 2-2 of FIG. 1, illustrating the membrane separating the first microchannel and the second microchannel.

FIGS. 1 and 2 illustrate one type of an organ-on-chip ("OOC") device 10. The OOC device 10 includes a body 12 that is typically comprised of an upper body segment 12a and a lower body segment 12b. The upper body segment 12a and the lower body segment 12b are preferably made of a polymeric material, such as Polydimethysyloxane (PDMS), PMMA, polycarbonate, COP/COC, polyurethane, SBS/SEBS, etc. The upper body segment 12a includes a first fluid inlet 14 and a second fluid inlet 24. A first fluid path for a first fluid includes the first fluid inlet 14, a first seeding channel 30, an upper microchannel 34, an exit channel 31, and then the first fluid outlet 24. A second fluid path for a second fluid includes the second fluid inlet 16, a first seeding channel 32, a lower microchannel 36, an outlet channel 33, and then the second fluid outlet 26.

As seen best in FIG. 2, a membrane 40 extends between the upper body segment 12a and the lower body segment 12b. The membrane 40 is preferably an inert polymeric membrane having uniformly or randomly distributed pores with sizes in the range from about 0.2 µm to about 12 µm in width. The membrane may, for example, be micro-molded, track-etched, laser-machined, fiber-based, or otherwise produced. The thickness of the membrane 40 is generally in the range of about of about 7 µm to about 100 µm. Preferably, the membrane 40 is made of a cured PDMS (poly-dimethylsiloxane). The membrane 40 separates the upper microchannel 34 from the lower microchannel 36 in an active region 37, which includes a bilayer of cells in the illustrated embodiment. In particular, a first cell layer 42 is adhered to a first side of the membrane 40, while a second cell layer 44 is adhered to a second side of the membrane 40. The first cell layer 42 may include the same type of cells as the second cell layer 44. Or the first cell layer 42 may include a different type of cell than the second cell layer 44. And while a single layer of cells is shown for the first cell layer 42 and the second cell layer 44, the first cell layer 42 and the second cell layer 44 may include multiple cell layers. Further, while the illustrated embodiment includes a bilayer of cells on the membrane 40, the membrane 40 may include only a single cell layer disposed on one of its sides.

The OOC device 10 is configured to simulate a biological function that typically includes cellular communication between the first cell layer 42 and the second cell layer 44, as would be experienced in-vivo within organs, tissues, cells, etc. Depending on the application, the membrane 40 is designed to have a porosity to permit the migration of cells, particulates, media, proteins, and/or chemicals between the upper microchannel 34 and the lower microchannel 36. The working fluids with the microchannels 34, 36 may be the same fluid or different fluids. As one example, as device 10 simulating a lung may have air as the fluid in one channel and a fluid simulating blood in the other channel. When developing the cell layers 42 and 44 on the membrane 40, the working fluids may be a tissue-culturing fluid.

In one embodiment, the active region 37 defined by the upper and lower microchannels 34, 36 has a length of less than about 10 cm, a height of less than 1.5 mm, and a width of less than 2000 µm. The OOC device 10 preferably includes an optical window that permits viewing of the fluids, media, particulates, etc. as they move across the first cell layer 42 and the second cell layer 44. Various image-gathering techniques, such as spectroscopy and microscopy, can be used to quantify and evaluate the effects of the fluid flow in the microchannels 34, 36, as well as cellular behavior and cellular communication through the membrane 40. More details on the OOC device 10 can be found in, for example, U.S. Pat. No. 8,647,861, which is owned by the assignee of the present application and is incorporated by reference in its entirety. Consistent with the disclosure in U.S. Pat. No. 8,647,861, in one preferred embodiment, the membrane 40 is capable of stretching and expanding in one or more planes to simulate the physiological effects of expansion and contraction forces that are commonly experienced by cells.

Figure 3:
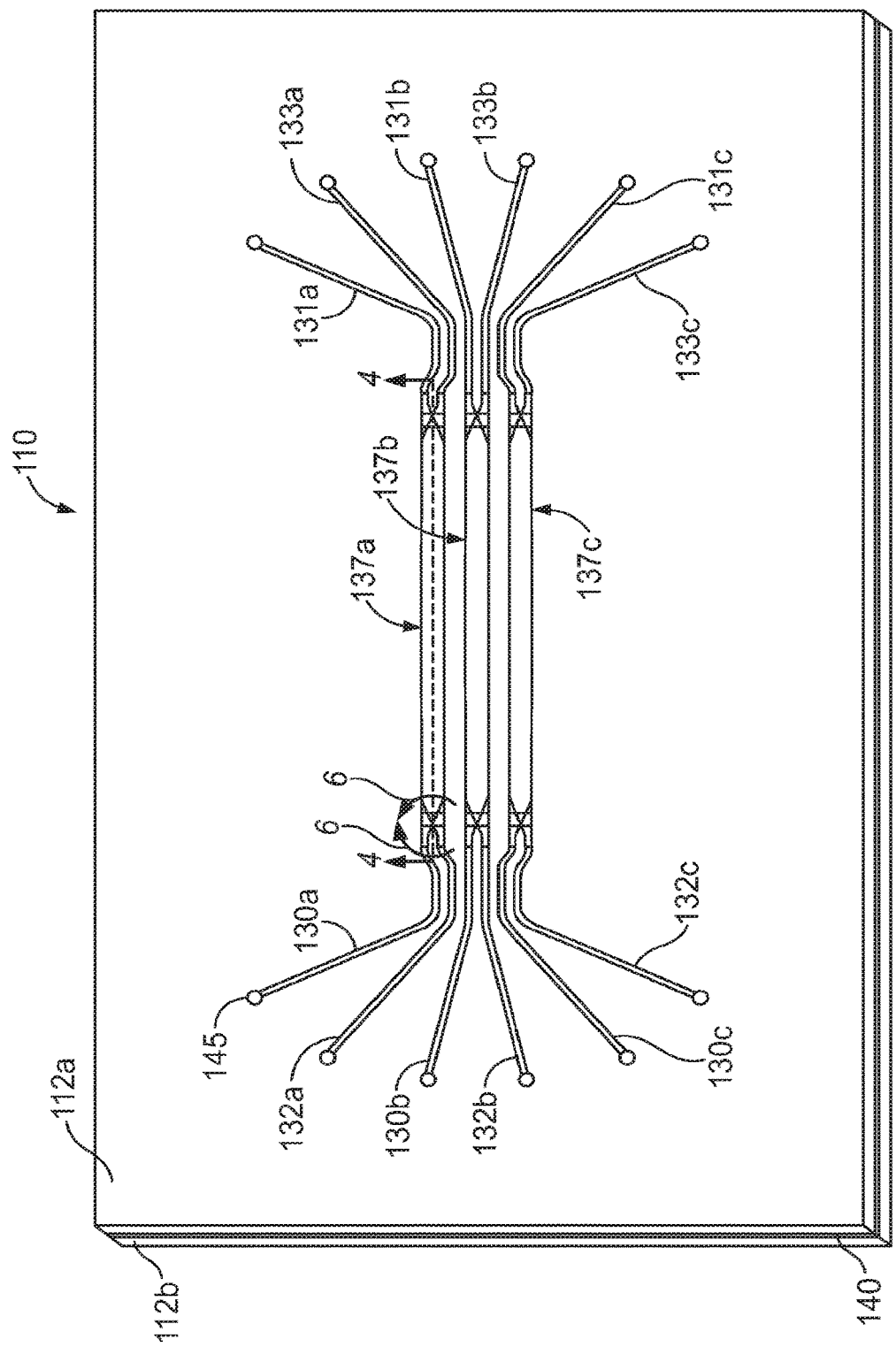
FIG. 3 illustrates another exemplary microfluidic device that includes multiple active regions that may be used with the present invention.

FIG. 3 illustrates an alternative OOC device 110 having a body 112 that is comprised of an upper body segment 112a and a lower body segment 112b. Unlike the embodiment of FIGS. 1-2, which has only a single pair of upper and lower microchannels 34, 36 that results in a single active region 37, the OOC device 112 includes three pairs of upper and lower microchannels, thereby producing three active regions 137a, 137b, 137c at which cells are tested or may interact with one another. Each upper seeding channel 130 on the left side of the OOC device 110 in the upper body segment 112a has a corresponding exit channel 131 on the right side in the upper body segment 112a. Each lower seeding channel 132 on the left side of the OOC device 110 in the lower body segment 112b has a corresponding exit channel 133 on the right side of the lower body segment 112b. Because of the multiple active regions 137, the upper seeding channels 130 and lower seeding channels 132 must be carefully designed so as to not overlap, as will be discussed in more detail below with reference to FIG. 6. Furthermore, the seeding channels 130, 132 are designed to have a higher flow rate (and more fluid shear force) than the microchannels in the active regions 137 to inhibit cellular attachment and growth within those seeding channels 130, 132.

Figure 4:
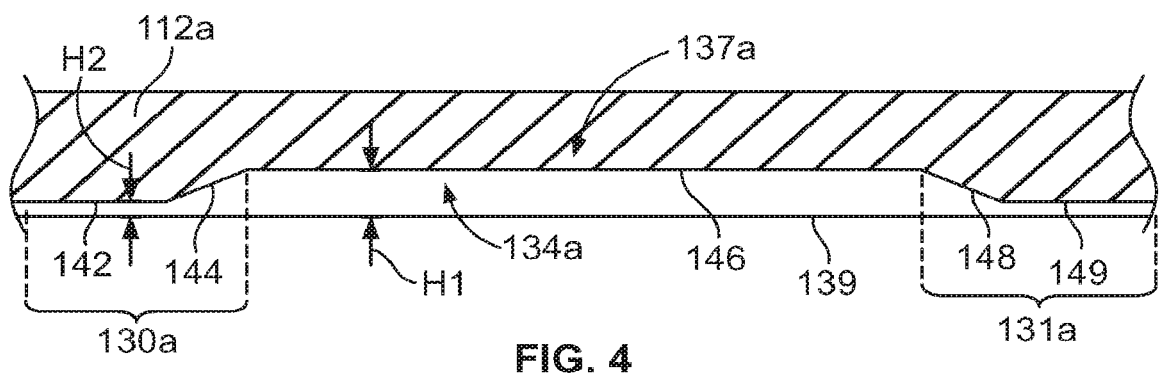
FIG. 4 is a cross-section of the microfluidic device taken along line 4-4 of FIG. 3, illustrating the relative heights of the microchannels and seeding channels.

FIG. 4 is a cross-section of the upper body segment 112a taken along line 4-4 in FIG. 3 to illustrate the geometric arrangements of the seeding channel 130a and the upper microchannel 134a, which are formed on a bottom surface 139 of the upper body segment 112a. In particular, the bottom surface 139 of the upper body segment 112a, which abuts against the membrane 140 (FIG. 3), includes a main seeding-channel surface 142 and a transition seeding-channel surface 144. The main seeding-channel surface 142 extends from the transition seeding-channel surface 144 to an inlet port 145 on the OOC device 110, which is shown in FIG. 3. In one preferred embodiment, input ports and outlet ports for the seeding channels 132 and exit channels, respectively, extend vertically from the exterior surface of the upper body segment 112a or the lower body segment 112b (or they may be segregated into inlet ports on one body segment, and outlet ports on the other body segment). The main seeding-channel surface 142 typically has one or more curved sections when viewed from the top (FIG. 3) so as to avoid intersection with any of the other five seeding channels 132a, 130b, 132b, 130c, 132c.

Fluid enters the inlet port 145, travels along the main seeding-channel surface 142, and then travels along the transition seeding-channel surface 144 before entering the active region 137a, where it travels along a top surface 146 of the microchannel 134a. As the fluid flows along this path, the lowermost boundary of the fluid path is defined by the membrane 140, which is sandwiched between the upper body segment 112a and the lower body segment 112b and abuts the lower surface 139 of the upper body segment 112a. The various channels can be formed in the upper body segment 112a and the lower body segment 112b through various processes, such as molding, etching, or micromachining.

In the active region 137a, the cross-sectional area of the microchannel 134a increases relative to the seeding channel 130a. The transition seeding-channel surface 144 serves to increase the height of the microchannel 134a relative to the seeding channel 130a. In particular, the microchannel 134a within the active region 137a has a height H1 as measured to the top surface 146 of the microchannel 134a, while the seeding channel 130a has a height H2, which is substantially smaller than the height H1. For example, the height H1 may be roughly 3 times (or more, such as 10 times) greater than the height H2. In one embodiment, the height H1 may be 1.0 mm and the height H2 may be 0.1 mm (100 µm). By having a decreased geometry within the seeding channel 130a, there is less surface area to which the cells may adhere. And, the fluidic shear force within the seeding channel 130a is substantially higher than the shear force within the microchannel 134a, as the shear force is inversely proportional to the square of the height of the fluid path. In other words, if the height H1 is 1 mm and the height H2 is 0.1 mm, the height change alone results in a 100-fold decrease in the shear force as the fluid enters the microchannel 134a.

Furthermore, the shear force can also be increased in the seeding channels without necessarily reducing the cross-sectional area. For example, in a channel with a rectangular cross-section and a height significantly smaller than the width, the shear is inversely proportional to height squared ($H^2$) and inversely proportional to the width. Hence, it is possible to maintain the same area, but increase the shear force by reducing the height. As such, the present invention contemplates altering the cross-sectional geometry of the channels, not necessarily only the cross-sectional area, to affect the shear force applied by the fluid.

As will be discussed below relative to FIG. 6, one or more of the opposing transverse surfaces on either side of the transition seeding-channel surface 144 may expand as well, providing geometric expansion of the fluid path's width and further decreasing the fluid velocity (and associated shear force) to a point where cell adhesion to the membrane 140 (or to other cells already adhered to the membrane 140) is encouraged. The present invention contemplates a beneficial reduction in the shear force within the microchannel 134a relative to the seeding channel through an increase in channel height, an increase in channel width, or a combination thereof within the microchannel 134a. Furthermore, the present invention contemplates, after a desired cell layer has been achieved on the membrane, choosing an increased flow rate for a tissue-culturing working fluid that substantially dislodges and washes away cells on walls within the seeding channel 130a while leaving the cellular layers on the membrane 140 in the active region 137 relatively undisturbed. The increased flow rate may result in a substantial turbulent flow in the seeding channel 130a to dislodge the cells, while only a laminar flow across at least a majority of the length of the microchannel 134a.

After the fluid leaves the active region 137a, it encounters a second transition surface 148, which leads to an exit-channel surface 149 that defines the geometry for the exit channel 131a. Accordingly, the fluid path decreases in geometry in this region, thereby resulting in an increased velocity as the fluid moves away from the active region 137a. The fluid path geometry defined by the second transition surface 148 and the exit-channel surface 149 does not necessarily need to be the same as the fluid path geometry defined by the transition seeding-channel surface 144 and the main seeding-channel surface 142. In some instances, it may be preferred to have a higher fluid velocity within the seeding channel 130a and a lower fluid velocity within the exit channel 131a, such as when sensors are placed in communication with fluid in the exit channel 131a to determine characteristics and/or constituents of the exiting fluid.

Figure 5:
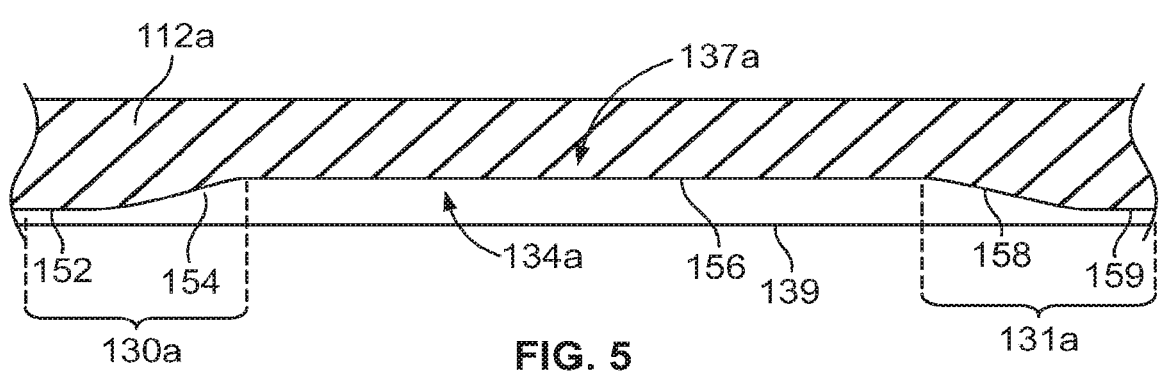
FIG. 5 is a cross-section of the microfluidic device having a different geometric configuration for the microchannels and seeding channels in FIG. 4.

FIG. 5 illustrates an alternative configuration for the seeding channel 130a, the microchannel 134a, and the exit channel 131a within the upper body segment 112a. Specifically, a main seeding-channel surface 152 gradually changes its shape to define a transition seeding-channel surface 154, which then gradually transitions into a top surface 156 of the microchannel 134a. Additionally, a second transition surface 158 extends downwardly from the top surface 156 and then extends gradually into the exit channel surface 159. Accordingly, the geometric changes associated with the seeding channel 130a, the microchannel 134a, and the exit channel 131a are smoother for the purpose of altering and controlling the fluid dynamics within those channels. For example, a relatively uniform laminar flow across the membrane 140 within the active region 137a may be desired for optimum cellular adherence to the membrane 140. The geometry transformations of the fluid path into the microchannel 134a can be designed to more readily change the high-shear flow within the seeding channel 130a to a relatively uniform laminar flow within the microchannel 134a. In doing so, cellular attachment to the walls within the seeding channel 130a can be substantially less than the attachment of the cells to the membrane 140. The cellular attachment is typically aided by the force of gravity. Accordingly, the present invention helps to keep the ratio of the cells within the cell layers in the active region 137 to the cells within the seeding channels 130 as high as possible.

While FIGS. 4-5 have been described relative to the upper seeding channel 130a and the microchannel 134a in the upper body segment 112a, it should be understood that the same or similar geometric path can be used relative to the corresponding lower seeding channel 132a and the lower microchannel 136a (FIG. 6), respectively, in the lower body segment 112b. In other words, both of the seeding channels 130a and 132a and the microchannels 134a, 136a may have the same or a similar cross-sectional geometry. Alternatively, the geometries of the microchannels 134a, 136a may be different to encourage different types of flows on either side of the membrane 140 within the active region 137a. The same is true of the upper exit channel 131a and the lower exit channel 133a (FIG. 3).

While the illustrated embodiment has been described relative to microfluidic devices comprising a membrane separating channels, other embodiments of the invention may not require a second channel. For example, the other side of the membrane can, for example, face a large cavity or an opening. Similarly, the design and method also allow embodiments without a membrane in the cell region (and thus without any requirement for a channel or cavity on an opposing side). Accordingly, some embodiments comprise a cell-culture region with at least one seeding channel.

Furthermore, it should be understood that the second active region 137b (FIG. 3) and its associated seeding channels, microchannels, and exit channels can be the same as, similar to, or substantially different from the corresponding channels within the first active region 137a, which have been described in detail above in FIGS. 4-5. Likewise, the third active region 137c (FIG. 3) and its associated seeding channels, microchannels, and exit channels may be the same as, similar to, or substantially different from the respective seeding channels, microchannels, and exit channels of the first and second active regions 137a and 137b.

In the embodiments using the high-shear seeding channels, there are a few different operational modes and configurations for the OOC device 10, 110. First, the fluid can move at a constant high rate, resulting in shear stresses that will inhibit (or prevent) cell adhesion within the high-shear seeding channels, while permitting cell adhesion in the lower-shear active regions of the microchannels. Second, the fluid can flow at a constant low rate, resulting in cell adhesion within the seeding channels and the microchannels. At some point after adequate cell adhesion has occurred in the active regions of the microchannels, the fluid flow rate is raised abruptly for a short period of time to increase the shear stress within the seeding channels, causing cells to be removed from (or detached from) the walls defining the seeding channels. However the increased fluid flow rate for the short period of time would not substantially affect cells adhered within the active regions of the microchannels. This second operational mode may be advantageous if the desired cell adhesion in the microchannels is not optimal due to the limited range of differential shear stresses that are attainable considering the fixed channel geometries and dimensions. Third, the channel dimensions of the OOC device 10, 110 are designed so that cells can either be (i) adhered within the microchannel while not adhering within the seeding channels, or (ii) allowed to adhere to and grow evenly within both the microchannel and seeding channels. However, an ultra-high abrupt shear stress would be generated to remove already adherent cells within the high-shear seeding channels, but without detaching the cells in the microchannel. This is different from the previous operational configuration because much higher shear stresses are required to detach cells that are already adhering to walls than to prevent suspended cells from attaching to the walls. Importantly, this third mode can be used in conjunction with the first or second operational modes to remove cells that spontaneously migrate into the high-shear seeding channels at a later point in time (e.g., days or weeks after the initial cell plating).

Preferably, the OOC device 10, 110 is designed with dimensions and geometric configurations that permit the function of all three operational modes by use of different flow rates (e.g., low, medium, and high flow rates). Of course, the amount of shear that is needed within a OOC device 10, 110 is dependent on the type of cells for the testing as well as the materials within the channels of the OOC device 10, 110 (i.e., cells will attach differently to different types of materials and also to existing cell layers). More information related to shear stress and adhesion of cells can be found in the following article: *Quantification of the adhesion strength of fibroblast cells on ethylene glycol terminated self-assembled monolayers by a microfluidic shear force assay*, Christophis et al., Phys. Chem. Chem. Phys., 12 (2010), pp. 4498-4504.

Figure 6:
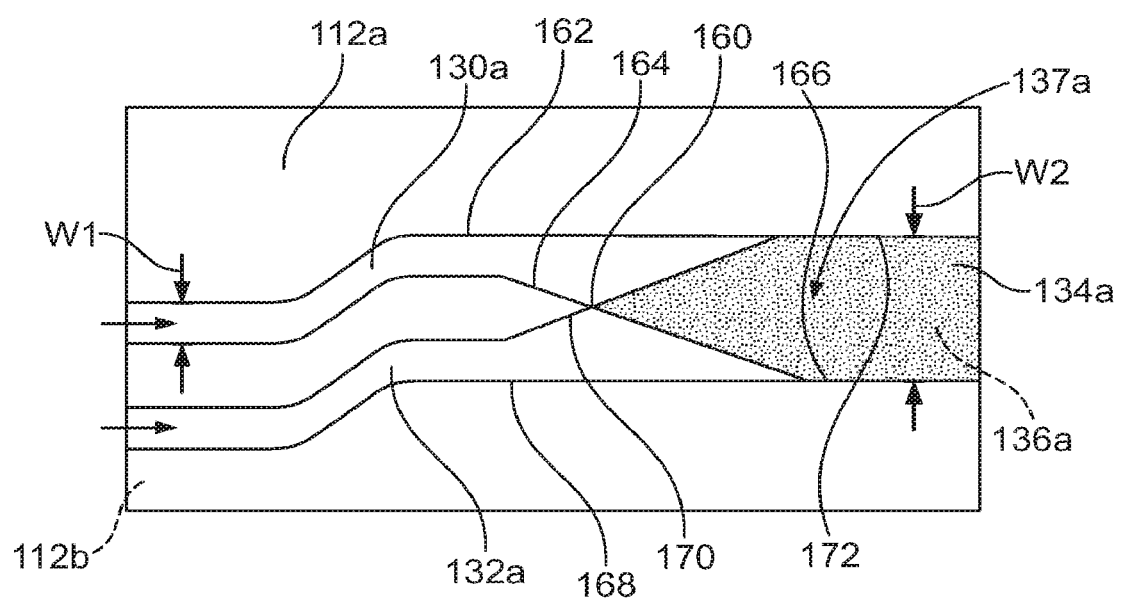
FIG. 6 is an enlarged view of the region of line 6-6 of FIG. 3, illustrating the offset fluid-path configuration for the pair of seeding channels of the microfluidic device of FIG. 3.

FIG. 6 is an enlarged view of the microfluidic device 110 in region 6-6 of FIG. 3, illustrating the offset fluid-path configurations for the pair of seeding channels 130a and 132a that lead to the first active region 137a in the microfluidic device 110. In this view (as in FIG. 3), the membrane 140 is transparent so that the lower fluid path within the lower body segment 112b below the membrane 140 and the upper fluid path within the upper body segment 112a above the membrane 140 can be visualized together. The first time that the lower fluid path and the upper fluid path are in fluidic communication is through the membrane 140 at a leading tip 160 of the active region 137a (shaded in FIG. 6), which is defined by the lower microchannel 136a and the upper microchannel 134a.

The first seeding channel 130a, which is associated with the upper microchannel 134a, is partially defined by a first lateral surface 162 that extends generally horizontally across the upper body segment 112a. The first seeding channel 130a is also partially defined by an angled surface 164 that extends generally downwardly before meeting a second lateral surface 166, both of which extend within the upper body segment 112a. As such, the fluid path associated with the upper microchannel 134a has a width "W1" in the seeding channel 130a and a width "W2" in the active region 137a. Furthermore, this expansion to the width W2 coincides with the expansion in the height of the seeding channel 130a that is brought about through the transition surface 144 (see transition between height H1 to height H2 in FIG. 4), such that the fluid path increases into two dimensions. This expansion in the width caused by the angled surface 164 provides for a decrease in velocity and associated fluid shear as the fluid moves into the upper microchannel 134a, which is defined on its four sides by the first lateral surface 162, the second lateral surface 166, the membrane 140, and the top surface 146 (FIG. 4). The decrease in the fluid shear force in the upper microchannel 134a helps to promote cellular attachment to the membrane 140 in the upper microchannel 134a, while the increased fluid shear force in the seeding channel 130a inhibits cellular attachment to the walls defining the seeding channel 130a.

The second seeding channel 132a is partially defined by a third lateral surface 168, which extends generally horizontally across the lower body segment 112b into the active region 137. The second seeding channel 132a is also partially defined by an angled surface 170 that extends generally upwardly at an angle before meeting a fourth lateral surface 172. The upper microchannel 136a is defined on four sides by the third lateral surface 168, the fourth lateral surface 172, the membrane 140, and a surface within the lower body segment 112b that opposes the membrane 140 (similar to the top surface 146 in the upper body segment 112a of FIG. 4). This expansion in the width caused by the angled surface 170 provides for a decrease in velocity and associated fluid shear as the fluid moves into the lower microchannel 136a.

Referring to both FIG. 3 and FIG. 6, the fluid path associated with the upper microchannel 134a overlaps with the fluid path associated with the lower microchannel 136a only in the active region 137a, where cells on either side of the membrane 140 are able to readily communicate with each other through the pores in the membrane 140, thereby allowing biochemical signals to pass from one side of the membrane 140 to the other (e.g., migration of cells, particulates, media, proteins, and/or chemicals through the porous membrane 140). All regions of the seeding channels 130a and 132a to the left of the leading tip 160 in FIG. 6 of the active region 137a (i.e., the unshaded regions) are still in contact with and defined by the membrane 140, which is sandwiched between the upper body segment 112a and the lower body segment 112b. But in those regions, there is no opposing fluid path on the opposing side of the membrane 140 to which cellular communication can be made; only an opposing solid surface of the respective upper body segment 112a or the lower body segment 112b is present in those fluid-path regions. It should be noted that the short lengths of the angled surfaces 164, 170 as the seeding channels 130a and 132a terminate at the upper microchannel 134a and the lower microchannel 136a help to minimize any cellular communication between the two fluid paths that are separated by membrane 140. In other words, by making the divergent regions of the seeding channels 130a and 132a as short as possible, cellular communication through the membrane 140 prior to the active region 137 is minimized.

The triangular-shaped entrance area of the active region 137a just to the right of the leading tip 160 is preferably as small as possible. This can be accomplished by increasing the angle between the angled surfaces 164, 170, such that flow paths of the seeding channels 130a and 132a are less aligned. However, there is a tradeoff in that it is preferable to avoid sharp turns in both fluid paths. Preferably, the angle between the angled surfaces 164, 170 is between about 30 degrees and 80 degrees.

By minimizing (or preferably eliminating) any potential leak paths between the seeding channels 130a and 130b, the present invention beneficially restricts the biological effects of cellular communication to the active region 137a at which experimental conditions are controlled and are properly monitored and/or imaged. This is particularly helpful in the case of an OOC device 110 having multiple seeding channels 130, 132 and exit channels 131, 133 to serve the active regions 137a, 137b, and 137c because these various fluid paths can be completely isolated from each other even though such a small space is used. As an example, the exemplary OOC device 110 has a width of 30 mm and a height of 55 mm. And while only three active regions 137a, 137b, and 137c are shown on the OOC device 110, it could accommodate ten or more active regions 137 and associated seeding channels and exit channels that do not overlap.

Figure 7:
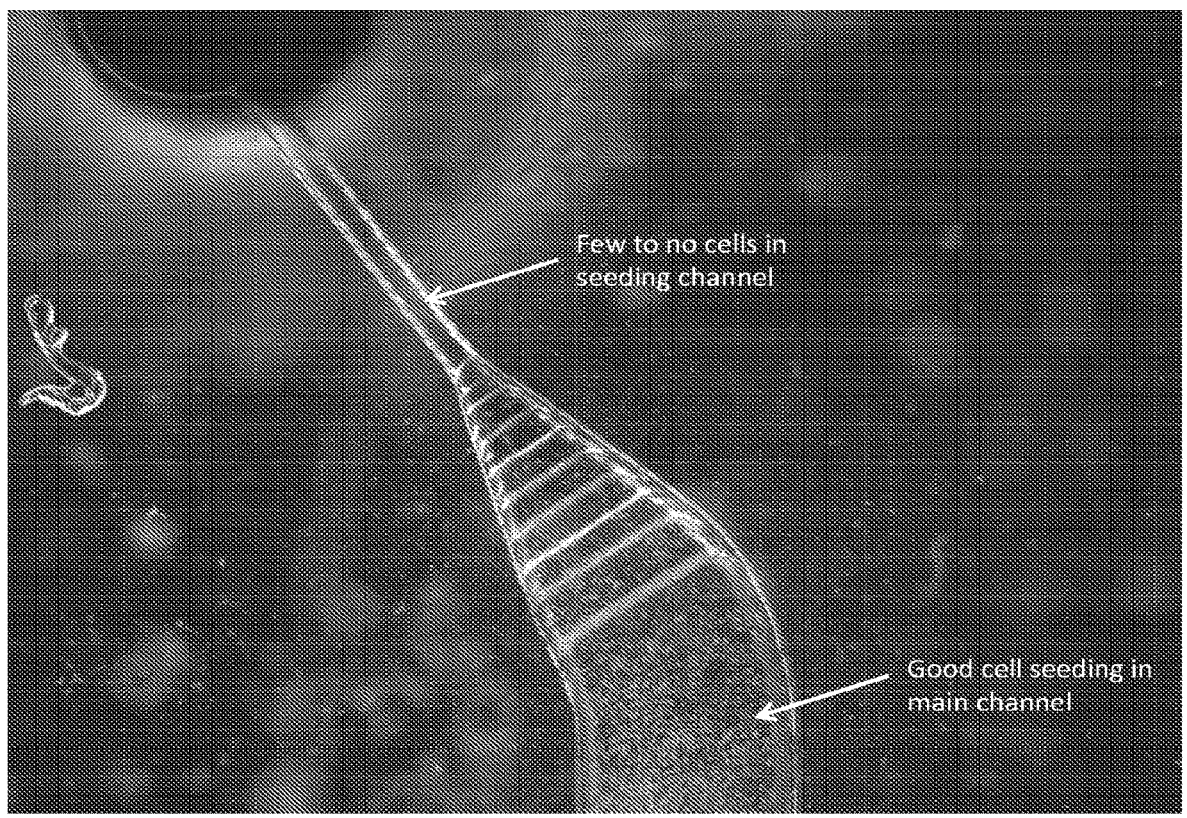
FIG. 7 illustrates an image of a microfluidic device made in accordance with the present invention in which the seeding channel has few to no cells, but the active region in the main microchannel has maintained an appropriate cell population.

FIG. 7 illustrates a phase contrast image of a microfluidic device made in accordance with the present invention in which the seeding channel has a different geometry than the active region of the microchannel. The transverse lines in the transition region where the seeding channel expands in dimension to the active region of the microchannel are due to manufacturing, which creates more of a "stair-step" expansion as opposed to a gradual, continuous expansion. In any event, the shear forces created by the fluid flow resulted in few to no cells being attached to the seeding channel, but the active region in the main microchannel maintained a good cell population. In this case, the OOC device was seeded with hepatocytes, which were allowed to begin attaching to surfaces in the seeding channel and the main channel. After cell attachment was identified, a flow rate of tissue-culture medium was introduced to the OOC device to remove cells from the seeding channel. As the image shows, this flow rate (by means of the shear force that the flow introduced) was successful in substantially clearing the cells from the seeding channel, whereas the cells in the main channel region remained fully seeded.

Furthermore, the present invention contemplates the method of using the OOC devices 10, 110 described above in a matter in which a flushing step is applied after the channels have been seeded. The increased shear forces in the seeding channels can be used to preferentially remove the cells from those seeding channels, while leaving the remaining cells located in the active region undisturbed. The removed cells would then exit the OOC devices 10, 110 from the exit channels 131, 133.

While the device 110 in FIG. 3 is illustrated as having multiple inlets and multiple outlets associated with the seeding channels 130, 132 and exit channels 131, 131, a single inlet with an associated manifold leading to the upper seeding channels 130 and a single inlet with an associated manifold leading to the lower seating channels 131 are also contemplated. Similarly, the exit channels 131 may lead into a common outlet, while the exit channels 133 may lead into a separate common outlet.

While the present invention has been described relative to an OOC device 10 having multiple microchannels on either side of the membrane, the unique geometries of the seeding channel and the microchannel can be applied to microfluidic devices having only a single fluid path, whereby only part of the path includes a cellular attachment region (e.g., a membrane, non-porous cell-attachment surface, etc.) that is preceded by a seeding region that feeds into the cellular attachment region.

For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation." Additionally, the singular terms "a," "an," and "the" include plural referents unless context clearly indicates otherwise.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein.

What is claimed is:

1. A method of reducing cells within a microfluidic device that includes a microchannel at least partially defined by a surface and a seeding channel for delivering fluids and cells to the surface, the microchannel having a first cross-sectional geometry, the seeding channel having a second cross-sectional geometry that is different from the first cross-sectional geometry, the method comprising:
   delivering cells through the seeding channel to the surface for a sufficient period of time to permit a layer of cells to adhere to the surface; and
   after the layer of cells has been achieved, introducing a fluid at a flow rate to produce a substantially higher shear force within the seeding channel to remove cells from the seeding channel while leaving the layer of cells on the surface undisturbed.

2. The method of claim 1, wherein the microchannel is at least partially defined by a membrane.

3. The method of claim 1, wherein the seeding channel includes a transition region that is directly connected to the microchannel, the transition region increases in area to the dimensions of the microchannel.

4. The method of claim 3, wherein the transition region is generally rectangular and increases in width.

5. The method of claim 3, wherein the transition region is generally rectangular and increases in height.

6. The method of claim 3, wherein the transition region changes dimensions gradually to promote a more laminar flow to the working fluid as the working fluid enters the microchannel.

7. A method of reducing cells within a microfluidic device that includes a microchannel at least partially defined by a surface and a seeding channel for delivering fluids and cells to the surface, the microchannel having a first cross-sectional geometry, the seeding channel having a second cross-sectional geometry that is different from the first cross-sectional geometry, the method comprising:
   delivering cells through the seeding channel to the surface for a sufficient period of time to permit a layer of cells to adhere to the surface; and
   after the layer of cells has been achieved, introducing a fluid at a flow rate to produce a substantially higher shear force within the seeding channel to preferentially remove cells from the seeding channel.

8. The method of claim 7, wherein the microchannel is at least partially defined by a membrane.

9. The method of claim 7, wherein the seeding channel includes a transition region that is directly connected to the microchannel, the transition region increases in area to the dimensions of the microchannel.

10. The method of claim 9, wherein the transition region is generally rectangular and increases in width.

11. The method of claim 9, wherein the transition region is generally rectangular and increases in height.

12. The method of claim 9, wherein the transition region changes dimensions gradually to promote a more laminar flow to the working fluid as the working fluid enters the microchannel.

* * * * *